(12) United States Patent
Stelea et al.

(10) Patent No.: US 7,951,182 B2
(45) Date of Patent: May 31, 2011

(54) SYSTEM AND METHOD FOR LEAK DETECTION IN EXTERNAL COOLING PAD

(75) Inventors: Stelica Stelea, Yorba Linda, CA (US); David Searl Kimball, Irvine, CA (US); Lynn Miyeko Shimada, Orange, CA (US); Kenneth A. Collins, Mission Viejo, CA (US); Grant Palmer, Irvine, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 1337 days.

(21) Appl. No.: 11/181,122

(22) Filed: Jul. 14, 2005

(65) Prior Publication Data

US 2007/0016270 A1    Jan. 18, 2007

(51) Int. Cl.
*A61F 7/08* (2006.01)

(52) U.S. Cl. ............. 607/104; 165/58; 607/108

(58) Field of Classification Search ........... 607/96, 607/104, 108, 109, 110, 111, 112, 114; 606/27; 36/2.6; 2/171.2, 458, 150–160, 209.13; 165/46, 165/11.1, 11.2, DIG. 8, DIG. 45, DIG. 46, 165/DIG. 47; 5/421
See application file for complete search history.

(56) References Cited

U.S. PATENT DOCUMENTS

| | | | | |
|---|---|---|---|---|
| 4,404,516 A | * | 9/1983 | Johnson, Jr. | 324/557 |
| 4,691,762 A | * | 9/1987 | Elkins et al. | 165/46 |
| 5,190,032 A | * | 3/1993 | Zacoi | 607/104 |
| 5,207,640 A | | 5/1993 | Hattler | 604/28 |
| 5,230,862 A | | 7/1993 | Berry et al. | 422/48 |
| 5,271,743 A | | 12/1993 | Hattler | 604/26 |
| 5,334,973 A | * | 8/1994 | Furr | 340/605 |
| 5,378,991 A | * | 1/1995 | Anderson et al. | 324/557 |
| 5,381,097 A | * | 1/1995 | Takatori et al. | 324/512 |
| 5,450,516 A | | 9/1995 | Pasquali et al. | 385/115 |
| 5,470,659 A | | 11/1995 | Baumgart et al. | 428/398 |
| 5,725,949 A | | 3/1998 | Pasquali et al. | 428/398 |
| 5,735,809 A | | 4/1998 | Gorsuch | 428/364 |
| 5,755,690 A | | 5/1998 | Saab | 604/96 |
| 5,837,003 A | | 11/1998 | Ginsburg | 607/106 |
| 5,876,667 A | | 3/1999 | Gremel et al. | 604/4 |
| 5,879,329 A | | 3/1999 | Ginsburg | 604/93 |
| 5,989,238 A | | 11/1999 | Ginsburg | 604/93 |
| 6,004,289 A | | 12/1999 | Saab | 604/96 |
| 6,019,783 A | | 2/2000 | Philips | 607/105 |
| 6,042,559 A | | 3/2000 | Dobak | 604/7 |
| 6,096,068 A | | 8/2000 | Dobak | 607/105 |
| 6,110,168 A | | 8/2000 | Ginsburg | 606/27 |
| 6,126,684 A | | 10/2000 | Gobin | 607/113 |
| 6,146,411 A | | 11/2000 | Noda | 607/105 |
| 6,149,670 A | | 11/2000 | Worthen | 607/3 |
| 6,149,673 A | | 11/2000 | Ginsburg | 607/96 |

(Continued)

OTHER PUBLICATIONS

Bay Plastics, Polyurethane (internet archive), http://web.archive.org/web/20030130203519/http://www/bayplastics.co.uk/Product+Materials/prod-polyurethane.htm, 2003.*

(Continued)

*Primary Examiner* — Henry M Johnson, III
(74) *Attorney, Agent, or Firm* — John L. Rogitz

(57) ABSTRACT

An externally-applied heat exchange pad has three layers laminated together, an inner and outer non-conductive layer and a middle conductive layer. A leak in the inner layer causes coolant to contact the middle layer and change impedance, which can be sensed and used as an indication of an impending total leak of the pad.

10 Claims, 1 Drawing Sheet

U.S. PATENT DOCUMENTS

| | | | | |
|---|---|---|---|---|
| 6,149,676 | A | 11/2000 | Ginsburg | 607/106 |
| 6,149,677 | A | 11/2000 | Dobak | 607/106 |
| 6,165,207 | A | 12/2000 | Balding | 607/105 |
| 6,178,562 | B1* | 1/2001 | Elkins | 2/458 |
| 6,197,045 | B1* | 3/2001 | Carson | 607/104 |
| 6,200,250 | B1* | 3/2001 | Janszen | 493/383 |
| 6,224,624 | B1 | 5/2001 | Lasheras | 607/105 |
| 6,231,594 | B1 | 5/2001 | Dae | 607/96 |
| 6,231,595 | B1 | 5/2001 | Dobak | 607/106 |
| 6,235,048 | B1 | 5/2001 | Dobak | 607/104 |
| 6,238,428 | B1 | 5/2001 | Werneth | 607/105 |
| 6,245,095 | B1 | 6/2001 | Dobak | 607/105 |
| 6,251,129 | B1 | 6/2001 | Dobak | 607/105 |
| 6,251,130 | B1 | 6/2001 | Dobak | 607/105 |
| 6,254,626 | B1 | 7/2001 | Dobak | 607/105 |
| 6,264,679 | B1 | 7/2001 | Keller | 607/105 |
| 6,287,326 | B1 | 9/2001 | Pecor | 607/105 |
| 6,290,717 | B1 | 9/2001 | Philips | 607/113 |
| 6,299,599 | B1 | 10/2001 | Pham | 604/113 |
| 6,306,161 | B1 | 10/2001 | Ginsburg | 607/106 |
| 6,312,452 | B1 | 11/2001 | Dobak | 607/105 |
| 6,325,818 | B1 | 12/2001 | Werneth | 607/105 |
| 6,338,727 | B1 | 1/2002 | Noda | 604/113 |
| 6,364,899 | B1 | 4/2002 | Dobak | 607/113 |
| 6,368,304 | B1 | 4/2002 | Aliberto | 604/113 |
| 6,375,674 | B1* | 4/2002 | Carson | 607/104 |
| 6,379,378 | B1 | 4/2002 | Werneth | 607/96 |
| 6,383,210 | B1 | 5/2002 | Magers | 607/105 |
| 6,393,320 | B2 | 5/2002 | Lasersohn | 607/3 |
| 6,405,080 | B1 | 6/2002 | Lasersohn | 607/3 |
| 6,409,747 | B1 | 6/2002 | Gobin | 607/113 |
| 6,416,533 | B1 | 7/2002 | Gobin | 607/113 |
| 6,419,643 | B1 | 7/2002 | Shimada | 600/323 |
| 6,428,563 | B1 | 8/2002 | Keller | 607/105 |
| 6,432,124 | B1 | 8/2002 | Worthen | 607/105 |
| 6,436,130 | B1 | 8/2002 | Philips | 607/105 |
| 6,436,131 | B1 | 8/2002 | Ginsburg | 607/106 |
| 6,440,158 | B1 | 8/2002 | Saab | 604/105 |
| 6,447,474 | B1 | 9/2002 | Balding | 604/66 |
| 6,450,987 | B1 | 9/2002 | Kramer | 604/523 |
| 6,450,990 | B1 | 9/2002 | Walker | 604/113 |
| 6,451,045 | B1 | 9/2002 | Walker | 607/105 |
| 6,454,792 | B1 | 9/2002 | Noda | 607/105 |
| 6,454,793 | B1 | 9/2002 | Evans | 607/105 |
| 6,458,150 | B1 | 10/2002 | Evans | 607/105 |
| 6,460,544 | B1 | 10/2002 | Worthen | 607/105 |
| 6,461,379 | B1* | 10/2002 | Carson et al. | 607/104 |
| 6,464,716 | B1 | 10/2002 | Dobak | 607/105 |
| 6,468,296 | B1 | 10/2002 | Dobak | 607/105 |
| 6,471,717 | B1 | 10/2002 | Dobak | 607/105 |
| 6,475,231 | B2 | 11/2002 | Dobak | 607/105 |
| 6,478,811 | B1 | 11/2002 | Dobak | 607/105 |
| 6,478,812 | B2 | 11/2002 | Dobak | 607/105 |
| 6,482,226 | B1 | 11/2002 | Dobak | 607/104 |
| 6,491,039 | B1 | 12/2002 | Dobak | 128/898 |
| 6,491,716 | B2 | 12/2002 | Dobak | 607/105 |
| 6,494,903 | B2 | 12/2002 | Pecor | 607/105 |
| 6,497,721 | B2 | 12/2002 | Ginsburg | 607/106 |
| 6,516,224 | B2 | 2/2003 | Lasersohn | 607/3 |
| 6,520,933 | B1 | 2/2003 | Evans | 604/103.7 |
| 6,527,798 | B2 | 3/2003 | Ginsburg | 607/106 |
| 6,529,775 | B2 | 3/2003 | Whitebook | 607/100 |
| 6,530,946 | B1 | 3/2003 | Noda | 607/113 |
| 6,533,804 | B2 | 3/2003 | Dobak | 607/105 |
| 6,540,771 | B2 | 4/2003 | Dobak | 607/105 |
| 6,544,282 | B1 | 4/2003 | Dae | 607/105 |
| 6,551,349 | B2 | 4/2003 | Lasheras | 607/105 |
| 6,554,797 | B1 | 4/2003 | Worthen | 604/113 |
| 6,558,412 | B2 | 5/2003 | Dobak | 607/105 |
| 6,572,538 | B2 | 6/2003 | Takase | 600/140 |
| 6,572,638 | B1 | 6/2003 | Dae et al. | 607/96 |
| 6,572,640 | B1 | 6/2003 | Balding | 607/105 |
| 6,576,001 | B2 | 6/2003 | Werneth | 607/96 |
| 6,576,002 | B2 | 6/2003 | Dobak | 607/105 |
| 6,581,403 | B2 | 6/2003 | Whitebook | 62/434 |
| 6,582,398 | B1 | 6/2003 | Worthen | 604/113 |
| 6,582,455 | B1 | 6/2003 | Dobak | 607/105 |
| 6,582,457 | B2 | 6/2003 | Dae | 607/113 |
| 6,585,692 | B1 | 7/2003 | Worthen | 604/113 |
| 6,585,752 | B2 | 7/2003 | Dobak | 607/105 |
| 6,589,271 | B1 | 7/2003 | Tzeng | 607/113 |
| 6,595,967 | B2 | 7/2003 | Kramer | 604/523 |
| 6,599,312 | B2 | 7/2003 | Dobak | 607/105 |
| 6,602,243 | B2 | 8/2003 | Noda | 604/544 |
| 6,602,276 | B2 | 8/2003 | Dobak | 607/105 |
| 6,607,517 | B1 | 8/2003 | Dae | 604/31 |
| 6,610,083 | B2 | 8/2003 | Keller | 607/105 |
| 6,620,130 | B1 | 9/2003 | Ginsburg | 604/113 |
| 6,620,131 | B2 | 9/2003 | Pham | 604/113 |
| 6,620,188 | B1 | 9/2003 | Ginsburg | 607/106 |
| 6,620,189 | B1 | 9/2003 | MacHold | 607/106 |
| 6,623,516 | B2 | 9/2003 | Saab | 607/105 |
| 6,635,076 | B1 | 10/2003 | Ginsburg | 607/106 |
| 6,641,602 | B2 | 11/2003 | Balding | 607/105 |
| 6,641,603 | B2 | 11/2003 | Walker | 607/105 |
| 6,645,232 | B2* | 11/2003 | Carson | 607/104 |
| 6,645,234 | B2 | 11/2003 | Evans | 607/113 |
| 6,648,905 | B2* | 11/2003 | Hoglund et al. | 607/104 |
| 6,648,906 | B2 | 11/2003 | Lasheras | 607/105 |
| 6,648,908 | B2 | 11/2003 | Dobak | 607/105 |
| 6,652,565 | B1 | 11/2003 | Shimada | 607/113 |
| 6,656,209 | B1 | 12/2003 | Ginsburg | 607/106 |
| 6,660,028 | B2 | 12/2003 | Magers | 607/105 |
| 6,669,715 | B2* | 12/2003 | Hoglund et al. | 607/104 |
| 6,673,098 | B1 | 1/2004 | Machold | 607/106 |
| 6,676,688 | B2 | 1/2004 | Dobak | 607/105 |
| 6,676,689 | B2 | 1/2004 | Dobak | 607/105 |
| 6,676,690 | B2 | 1/2004 | Werneth | 607/105 |
| 6,679,906 | B2 | 1/2004 | Hammack | 607/105 |
| 6,679,907 | B2 | 1/2004 | Dobak | 607/105 |
| 6,682,551 | B1 | 1/2004 | Worthen | 607/105 |
| 6,685,732 | B2 | 2/2004 | Kramer | 607/106 |
| 6,685,733 | B1 | 2/2004 | Dae | 607/105 |
| 6,692,488 | B2 | 2/2004 | Dobak | 606/21 |
| 6,692,518 | B2* | 2/2004 | Carson | 607/104 |
| 6,692,519 | B1 | 2/2004 | Hayes | 607/105 |
| 6,695,873 | B2 | 2/2004 | Dobak | 607/105 |
| 6,695,874 | B2 | 2/2004 | MacHold | 607/106 |
| 6,699,268 | B2 | 3/2004 | Kordis | 607/113 |
| 6,702,783 | B1 | 3/2004 | Dae | 604/113 |
| 6,702,839 | B1 | 3/2004 | Dae | 607/96 |
| 6,702,840 | B2 | 3/2004 | Keller | 607/105 |
| 6,702,841 | B2 | 3/2004 | Nest | 607/105 |
| 6,702,842 | B2 | 3/2004 | Dobak | 607/105 |
| 6,706,060 | B2 | 3/2004 | Tzeng | 607/105 |
| 6,709,448 | B2 | 3/2004 | Walker | 607/105 |
| 6,716,188 | B2 | 4/2004 | Noda | 604/6.13 |
| 6,716,236 | B1 | 4/2004 | Tzeng | 607/113 |
| 6,719,723 | B2 | 4/2004 | Werneth | 604/113 |
| 6,719,724 | B1 | 4/2004 | Walker | 604/113 |
| 6,719,779 | B2 | 4/2004 | Daoud | 607/105 |
| 6,726,653 | B2 | 4/2004 | Noda | 604/113 |
| 6,726,708 | B2 | 4/2004 | Lasheras | 607/105 |
| 6,726,710 | B2 | 4/2004 | Worthen | 607/105 |
| 6,733,517 | B1 | 5/2004 | Collins | 607/105 |
| 6,740,109 | B2 | 5/2004 | Dobak | 607/105 |
| 6,749,585 | B2 | 6/2004 | Aliberto | 604/113 |
| 6,749,625 | B2 | 6/2004 | Pompa | 607/105 |
| 6,752,786 | B2 | 6/2004 | Callister | 604/113 |
| 6,755,850 | B2 | 6/2004 | Dobak | 607/104 |
| 6,755,851 | B2 | 6/2004 | Noda | 607/113 |
| 6,799,063 | B2* | 9/2004 | Carson | 600/372 |
| 2001/0007951 | A1 | 7/2001 | Dobak | 607/106 |
| 2001/0016764 | A1 | 8/2001 | Dobak, III | 607/105 |
| 2001/0041923 | A1 | 11/2001 | Dobak | 607/105 |
| 2002/0007203 | A1 | 1/2002 | Gilmartin | 607/105 |
| 2002/0016621 | A1 | 2/2002 | Werneth | 607/96 |
| 2002/0068964 | A1 | 6/2002 | Dobak | 607/113 |
| 2002/0077680 | A1 | 6/2002 | Noda | 600/549 |
| 2002/0091429 | A1 | 7/2002 | Dobak | 607/105 |
| 2002/0111616 | A1 | 8/2002 | Dea | 606/27 |
| 2002/0151946 | A1 | 10/2002 | Dobak, III | 607/105 |
| 2002/0177804 | A1 | 11/2002 | Saab | 607/105 |
| 2002/0183692 | A1 | 12/2002 | Callister | 604/113 |
| 2002/0193738 | A1 | 12/2002 | Adzich | 604/113 |
| 2002/0193853 | A1 | 12/2002 | Worthen | 607/3 |
| 2002/0193854 | A1 | 12/2002 | Dobak | 607/105 |

| | | |
|---|---|---|
| 2003/0078641 A1 | 4/2003 | Dobak .......................... 607/105 |
| 2003/0114835 A1 | 6/2003 | Noda ........................... 604/544 |
| 2003/0144714 A1 | 7/2003 | Dobak .......................... 607/104 |
| 2003/0187489 A1 | 10/2003 | Dobak .......................... 607/105 |
| 2003/0195465 A1 | 10/2003 | Worthen ....................... 604/113 |
| 2003/0195466 A1 | 10/2003 | Pham ........................... 604/113 |
| 2003/0195597 A1 | 10/2003 | Keller .......................... 607/105 |
| 2003/0216799 A1 | 11/2003 | Worthen ........................ 606/27 |
| 2003/0225336 A1 | 12/2003 | Callister ...................... 600/505 |
| 2004/0034399 A1 | 2/2004 | Ginsburg ..................... 607/106 |
| 2004/0039431 A1 | 2/2004 | Machold |
| 2004/0044388 A1 | 3/2004 | Pham ........................... 607/105 |
| 2004/0050154 A1 | 3/2004 | Machold |
| 2004/0054325 A1 | 3/2004 | Ginsburg ..................... 604/113 |
| 2004/0073280 A1 | 4/2004 | Dae |
| 2004/0078014 A1* | 4/2004 | Shapira ........................ 604/361 |
| 2004/0087934 A1 | 5/2004 | Dobak |
| 2004/0102825 A1 | 5/2004 | Daoud |
| 2004/0102826 A1 | 5/2004 | Lasheras |
| 2004/0102827 A1 | 5/2004 | Werneth |
| 2004/0106969 A1 | 6/2004 | Dobak |
| 2004/0111138 A1 | 6/2004 | Bleam .......................... 607/105 |
| 2004/0116987 A1 | 6/2004 | Magers |
| 2004/0116988 A1 | 6/2004 | Hammack |
| 2004/0122527 A1* | 6/2004 | Imran ........................ 623/23.67 |
| 2004/0127851 A1 | 7/2004 | Noda ............................ 604/503 |
| 2005/0065584 A1* | 3/2005 | Schiff et al. .................. 607/105 |
| 2006/0187638 A1* | 8/2006 | Vinson et al. ................. 361/698 |

OTHER PUBLICATIONS

U.S. Appl. No. 60/272,442, Worthen et al.

* cited by examiner

SYSTEM AND METHOD FOR LEAK DETECTION IN EXTERNAL COOLING PAD

Field of the Invention

The present invention relates generally to patient temperature control using externally-applied devices.

Background of the Invention

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high intracranial pressure. The present assignee has covered one or more of the above treatments using an intravascular heat exchange catheter in U.S. Pat. Nos. 6,149,670, 6,290,717, 6,432,124, 6,454,793, 6,682,551, and 6,726,710 (collectively, "the Alsius treatment patents"), all of which are incorporated herein by reference.

Less optimally, external patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference. Because such systems are used, the present invention recognizes the need to detect impending coolant leaks in the applied pads to avoid such leaks, so that patient discomfort and system malfunction are avoided before they occur.

SUMMARY OF THE INVENTION

A heat exchange pad configured for placement against the skin of a patient to exchange heat with the patient includes an outer envelope. The outer envelope includes an outer layer made of a high dielectric material such that any electrical discharge in the pad is effectively blocked from passing through the outer layer to the patient. Also, the envelope has an inner layer. A middle layer is sandwiched between the inner and outer layers and is made of a relatively electrically conductive material. The middle layer is electrically connected to a control system associated with the pad.

If desired, the layers can be laminated together. In some embodiments, in the event of a rupture in the inner layer, coolant in the pad contacts the middle layer to establish a change in impedance that may be sensed by the control system. In specific embodiments an impedance between the middle layer and the coolant can be used as an indication as to whether a leak exists. More particularly, in some implementations a drop in impedance can indicate that a leak is in the inner layer. The inner layer may be made of the same material as the outer layer, and the middle layer may be foil or plastic impregnated with conductive material.

In another aspect, a patient temperature control system includes at least one pad positionable against the skin of a patient to exchange heat therewith, and a control system engaged with the pad to circulate coolant therethrough to establish a desired temperature. Means are provided on the pad for providing early warning of a complete loss of integrity of the pad before it occurs.

In still another aspect, a method for providing an alarm that indicates an impending loss of fluid integrity of a heat exchange pad engageable with the exterior of a patient before fluid in the pad leaks out of the pad onto the patient includes receiving a signal from the pad representing an impedance. If the signal satisfies a leakage threshold, an alarm is activated.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
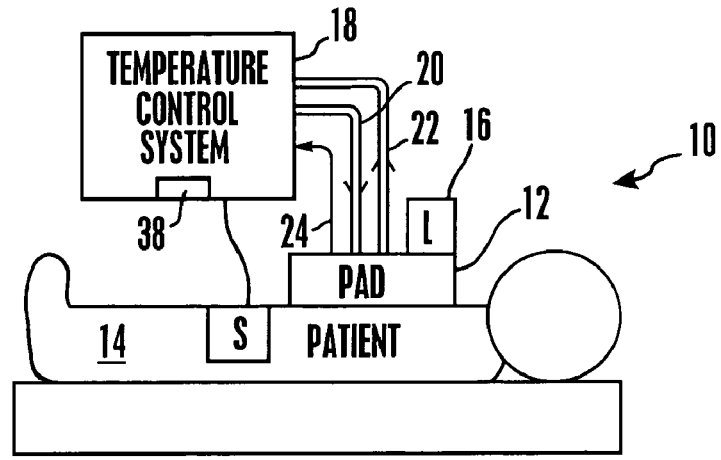
FIG. 1 is a schematic view of a non-limiting system in accordance with the present invention.

Referring initially to FIG. 1, a system is shown, generally designated 10, that includes one or more pads 12 that are positioned against the external skin of a patient 14 (only one pad 12 shown for clarity). The pad 12 may be any one of the pads disclosed in the external pad patents or it may be any other type of external heat exchange pads, as modified as disclosed herein in reference to FIG. 2. A substrate 16 such as a label that is affixed to the pad or an instruction manual that accompanies the pad can also be provided that bears instructions for use. In any case, the temperature of the pad 12 can be controlled by a controller 18 receiving a patient temperature signal from one or more temperature sensors "S" in accordance with principles set forth in the external pad patents to exchange heat with the patient 14, including to establish normothermia in a febrile patient and to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. Patient warming can also be effected using the pad 12 for, e.g., re-warming after surgery.

Heat exchange fluid, referred to herein as "coolant" regardless of its temperature, is circulated from the control system 18, through a supply line 20 to the pad 12, through various internal coolant circulation structure within the pad 12, e.g., the structures disclosed in the pad patents, and back through a return line 22 to the control system 18 for heating or cooling as needed for the particular application. Electrical leads 24, e.g., two, can be provided with one lead 24 extending between the external three-ply case of the pad 12 and the control system 18 and the other lead 24 extending between the interior coolant space of the pad 24 and the control system 18, for purposes to be shortly disclosed in relation to FIG. 2. A pump in or associated with the control system 18 may be engaged with the coolant supply line 20 to push coolant through the pad 12, or the pump may be engaged with the coolant return line 22 to suck coolant through the pad 12.

Figure 2:
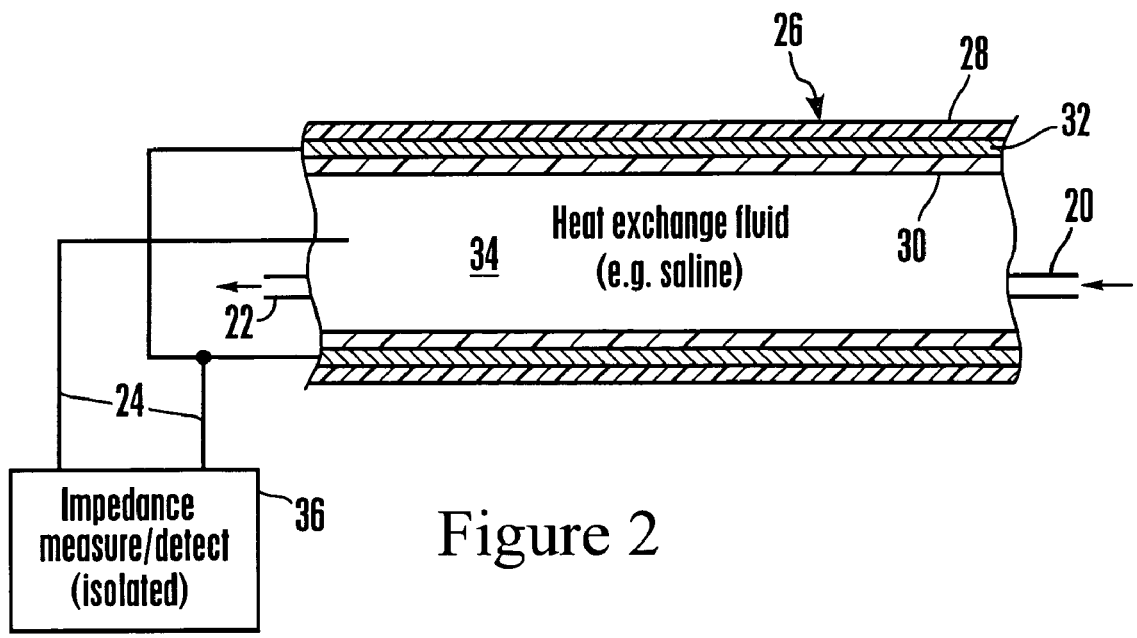
FIG. 2 is a cross-section of a non-limiting embodiment of the present external heat exchange pad.

FIG. 2 shows details of the invention. The pad 12 includes an outer envelope 26 that holds internal coolant circulation structure, which is omitted in FIG. 2 for clarity of disclosure. The outer envelope 26 is three-ply at least. Specifically, the envelope 26 includes an outer layer 28 made of a high dielectric material so that any electrical discharge in the pad 12 is effectively blocked from passing through the outer layer 28 to the patient, it being understood that the outer layer 28 is disposed against the skin of the patient perhaps with a gel or liquid interposed between it and the skin. The envelope 26 also has an inner layer 30 that may be made of the same material as the outer layer 28. A middle layer 32 is sandwiched between the inner and outer layers 30, 28. The middle layer 32 may be made of a relatively electrically conductive material, e.g., foil, or plastic impregnated with sufficient conductive material, or other appropriate material, and it is electrically connected to one of the electrical leads 24 and, hence, to the control system 18. The other lead extends between the control system 18 and interior coolant space 34 of the pad 12 as shown. The layers 28, 30, 32 preferably are laminated together or otherwise held together against each adjacent layer.

The point is that the middle layer 32 is sufficiently conductive such that in the event of a rupture in the inner layer 30, coolant contacts the middle layer 32 to establish a change in impedance that is sensed by an impedance measurement/detector system 36 through the leads 24. The impedance measurement/detector system 36 may be part of the control system 18 shown in FIG. 1.

For instance, the impedance between the middle layer 32 and the coolant may be measured through the leads 24 as an indication as to whether a leak exists. As an example, a significant drop in impedance can indicate a leak in the inner layer 30, making a leak through all three layers more likely than otherwise and, hence, providing early warning of such a complete loss of integrity of the pad 12 before it occurs. Accordingly, the control system 18 may activate an audible and/or visual alarm 38 (FIG. 1) to alert personnel of an impending leak. The same principles can be applied to determining whether the liquid or gel, if used, that is between the patient and pad is leaking through a hole in the outer layer to the middle layer.

While the particular SYSTEM AND METHOD FOR LEAK DETECTION IN EXTERNAL COOLING PAD as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". It is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. Absent express definitions herein, claim terms are to be given all ordinary and accustomed meanings that are not irreconcilable with the present specification and file history.

What is claimed is:

1. A heat exchange pad, comprising:
   an outer envelope configured for placement against the skin of a patient to exchange heat therewith and including:
   an outer layer made of a high dielectric material such that any electrical discharge in the pad is effectively blocked from passing through the outer layer to the patient;
   an inner layer; and
   a middle layer sandwiched between the inner and layers and made of a relatively electrically conductive material, the middle layer being electrically connected to a control system associated with the pad.

2. The pad of claim 1, wherein the layers are laminated together.

3. The pad of claim 1, wherein in the event of a rupture in the inner layer, coolant in the pad contacts the middle layer to establish a change in impedance that is sensed by the control system.

4. The pad of claim 3, wherein an impedance between the middle layer and the coolant is used as an indication as to whether a leak exists.

5. The pad of claim 4, wherein a drop in impedance indicates a leak in the inner layer.

6. The pad of claim 1, wherein the inner layer is made of the same material as the outer layer.

7. The pad of claim 1, wherein the middle layer is made of foil.

8. The pad of claim 1, wherein the middle layer is made of plastic impregnated with conductive material.

9. A method for providing an alarm indicating an impending loss of fluid integrity of a heat exchange pad engageable with the exterior of a patient before fluid in the pad leaks out of the pad onto the patient, comprising:
   receiving a signal from the pad representing an impedance; and
   if the signal satisfies a leakage threshold, activating an alarm.

10. The method of claim 9, wherein the impedance at least in part is related to a middle conductive layer sandwiched between two non-conductive layers of an envelope of the pad.

* * * * *